United States Patent [19]

Heimann

[11] 4,216,860
[45] Aug. 12, 1980

[54] MEDICAL DEVICE CONTAINER AND METHOD OF MANUFACTURE

[75] Inventor: Lester Heimann, Somerset, N.J.
[73] Assignee: Electro-Catheter Corporation, Rahway, N.J.
[21] Appl. No.: 968,342
[22] Filed: Dec. 11, 1978
[51] Int. Cl.² .................. B65D 85/20; A61B 19/00
[52] U.S. Cl. ........................ 206/370; 206/523; 206/565; 206/572
[58] Field of Search ............. 53/420, 425–426, 53/453–454, 477; 206/363–364, 370, 430, 440, 461, 467, 470–473, 477–478, 483–484.1, 521, 523, 565, 591–592

[56] References Cited

U.S. PATENT DOCUMENTS

| | | | |
|---|---|---|---|
| 2,319,556 | 5/1943 | Rhein | 206/485 X |
| 2,557,794 | 6/1951 | Nicolle | 206/484 |
| 2,645,334 | 7/1953 | Aldridge | 206/306 |
| 3,035,691 | 5/1962 | Rasmussen et al. | 206/364 |
| 3,353,664 | 11/1967 | Armentrout et al. | 206/461 X |
| 3,696,920 | 10/1972 | Lahay | 206/370 |
| 3,750,875 | 8/1973 | Juster | 206/364 |
| 4,019,633 | 4/1977 | Roth | 206/364 |

FOREIGN PATENT DOCUMENTS 1238428  7/1960  France ..................... 206/461

Primary Examiner—William T. Dixson, Jr.
Attorney, Agent, or Firm—Lackenbach, Lilling & Siegel

[57] ABSTRACT

An improved medical device container and method of manufacture thereof, wherein the container is adapted to be opened manually and dispense the contents onto a sterile field without the need of manual contact. The container is a thermally formed blister package and features a tray having at least one depression which is sized and shaped to receive a sterile medical appliance, and a pliable backing sheet having at least one flexible insert affixed thereto. The backing sheet is bonded to the periphery of the tray, and the insert engages the medical device and urges it into firm contact with a portion of the depression to secure the device therein. The backing sheet is adapted to be manually peeled away from the tray and thereby pull the flexible insert out of the depression so that the medical device may fall freely onto a sterile location without the need for manual contact.

9 Claims, 7 Drawing Figures

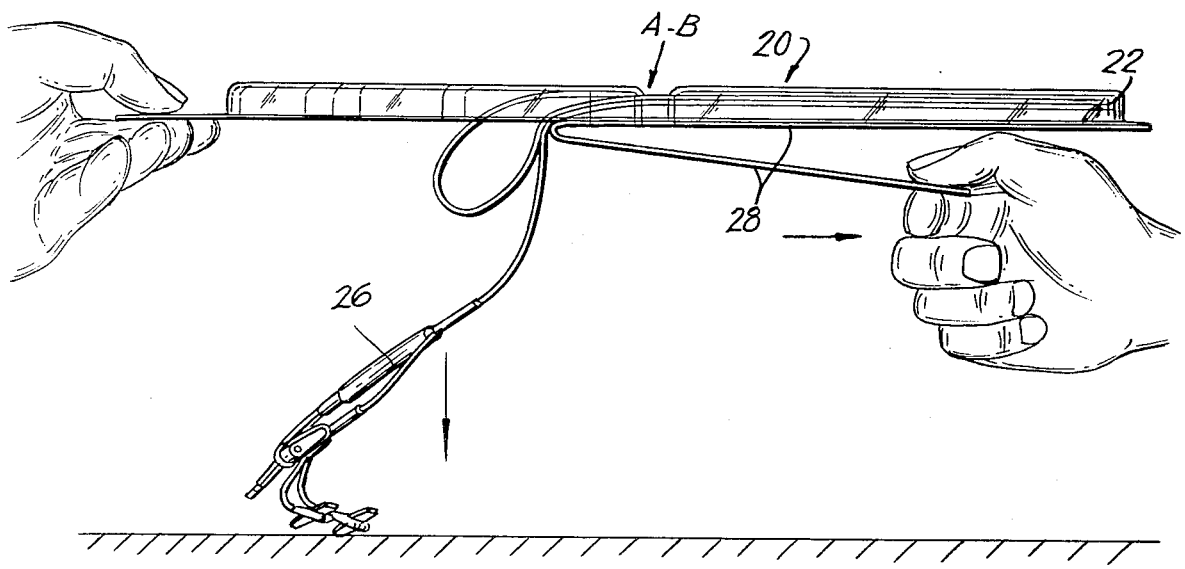
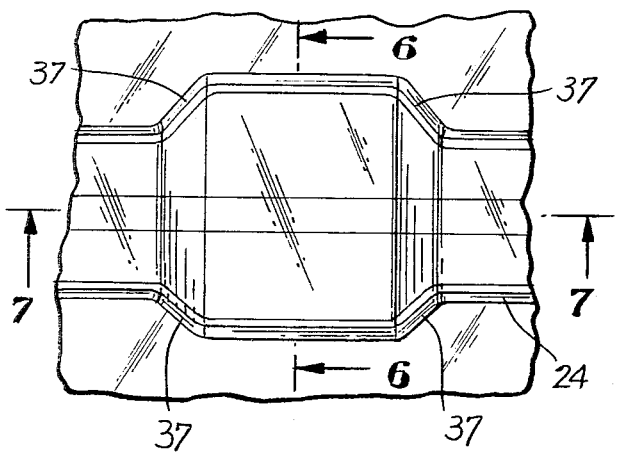
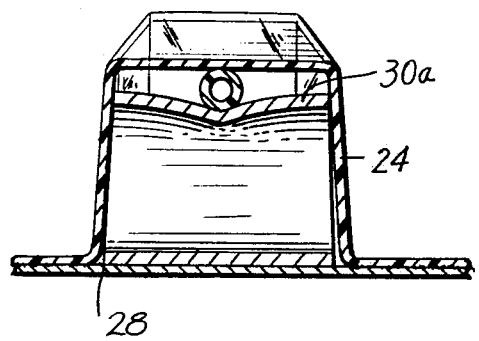
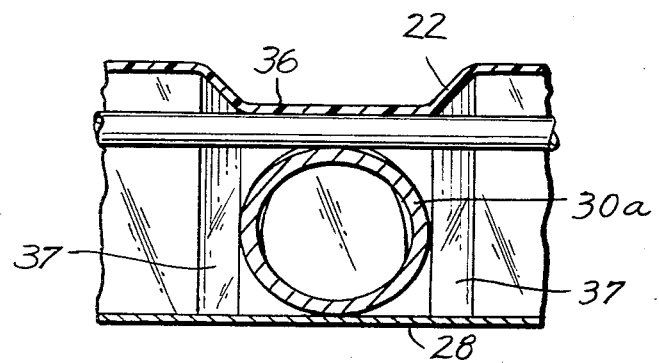

MEDICAL DEVICE CONTAINER AND METHOD OF MANUFACTURE

BACKGROUND OF THE INVENTION

1. Field of the Invention

The present invention relates to an improved medical device container and method of manufacture thereof, and more particularly to thermally formed blister package for containing sterile medical devices or appliances which container allows the contents to be placed onto a horizontal surface without the need for manual contact. The method of manufacture provides for the thermal bonding of at least one insert to a flexible backing sheet simultaneously with the bonding of the backing sheet to the tray.

2. Description of the Prior Art

Various types of medical device containers have been used in the past to transport and contain medical devices such as catheters and the like, which containers necessitated manual removal of the contents by lifting or pulling the contents out of the container.

The following prior art U.S. Pat. Nos. show various prior packages or containers which might be suitable for pharmaceutical or surgical objects: 2,557,794, 3,338,400, 3,696,920, and 3,830, 365.

U.S. Pat. No. 2,557,794 is directed to a pharmaceutical package where two mating sheets are bonded together with a pellet or some other product held in a product cavity of the top sheet by a protrusion formed in the bottom mating sheet.

U.S. Pat. No. 3,830,365 is directed to a vacuum skin package where the tray has protrusions which support an article in the product cavity.

U.S. Pat. No 3,696,920 discloses an envelope package for surgical instruments comprising a tray and plastic top cover which is stripable from the tray, and U.S. Pat. No. 3,338,400 discloses a sterile package for surgical articles where the tray has a separate bridge for holding the articles on the tray and in the product cavity.

As is readily apparent, the prior art does not show or suggest, taken singly or in combination, the structure of the present invention.

SUMMARY OF THE INVENTION

The present invention overcomes the disadvantages of the prior art containers by providing an improved medical device container in the form of a blister package such that the backing sheet may be removed or peeled away from the retaining tray, along with the attached inserts, so that the workpiece contained therein may fall freely, without manual manipulations onto a sterile field. The package features at least one flexible insert bonded to the backing sheet to retain the workpiece within the container prior to removal, which insert releases the product with the separation of the tray from the flexible backing.

The structure of the present invention includes a tray having at least one depression sized and shaped to receive a medical device, a flexible backing sheet which is bonded to said tray at least at the outer periphery of the tray which is adapted to hermetically seal the medical device within the container, and at least one flexible insert which is bonded to the backing sheet and disposed in the depression to secure the medical device therein. The insert is pulled away from the depression, allowing the medical device to fall freely from the tray when the backing sheet is peeled therefrom, and manual handling of the sterile device prior to use is eliminated by the present invention. The method of manufacture features forming at least one depression in a tray which is shaped to receive a medical device, and bonding at least one flexible insert to the face of a flexible backing sheet which engages the tray simultaneously with the bonding of the backing sheet onto the tray.

It is an object of the present invention to provide a container which may be easily handled and opened, and which will allow the workpiece contained therein to fall freely onto a sterile field without manual handling.

Furthermore, it is an object of the present invention to provide a medical device container which includes a tray of a thermoplastic material, and which tray is tinted to prevent the transmission of ultraviolet light therethrough.

Another object of the present invention is to provide a medical device container which facilitates rapid removal of the contents therefrom and which will adequately support and protect the contents during shipment.

Yet still another object of the present invention is to provide a method of manufacturing a medical container which includes bonding a flexible insert to a backing sheet during the bonding of the backing to the supporting tray of a blister package.

Still further objects and features of the present invention reside in the provision of an improved medical device container and method of manufacture thereof, which is simple in construction, inexpensive to manufacture, and thereby permitting wide use and distribution.

Another object of the package is that it incorporates a membrane which enables gas sterilization. The package may be sterilized by any conventional means including steam and radiation.

These, together with the various ancillary objects and features of the invention which will become apparent as the following description proceeds, are attained by the medical device container and method of manufacture, preferred embodiments of which are shown in the accompanying drawings, by way of example only, wherein:

BRIEF DESCRIPTION OF THE DRAWINGS

FIG. 4 is a side elevational view thereof showing the backing sheet being peeled away from the supporting tray and the workpiece falling freely therefrom;

FIG. 5 is a top plan view of a portion of the depression adapted to receive the flexible insert;

FIG. 6 is a partial vertical cross-sectional view taken along the plane of line 6—6 in FIG. 5; and FIG. 7 is a partial vertical cross-sectional view taken along the plane of line 7—7 in FIG. 5.

DETAILED DESCRIPTION OF THE INVENTION

Figure 1:
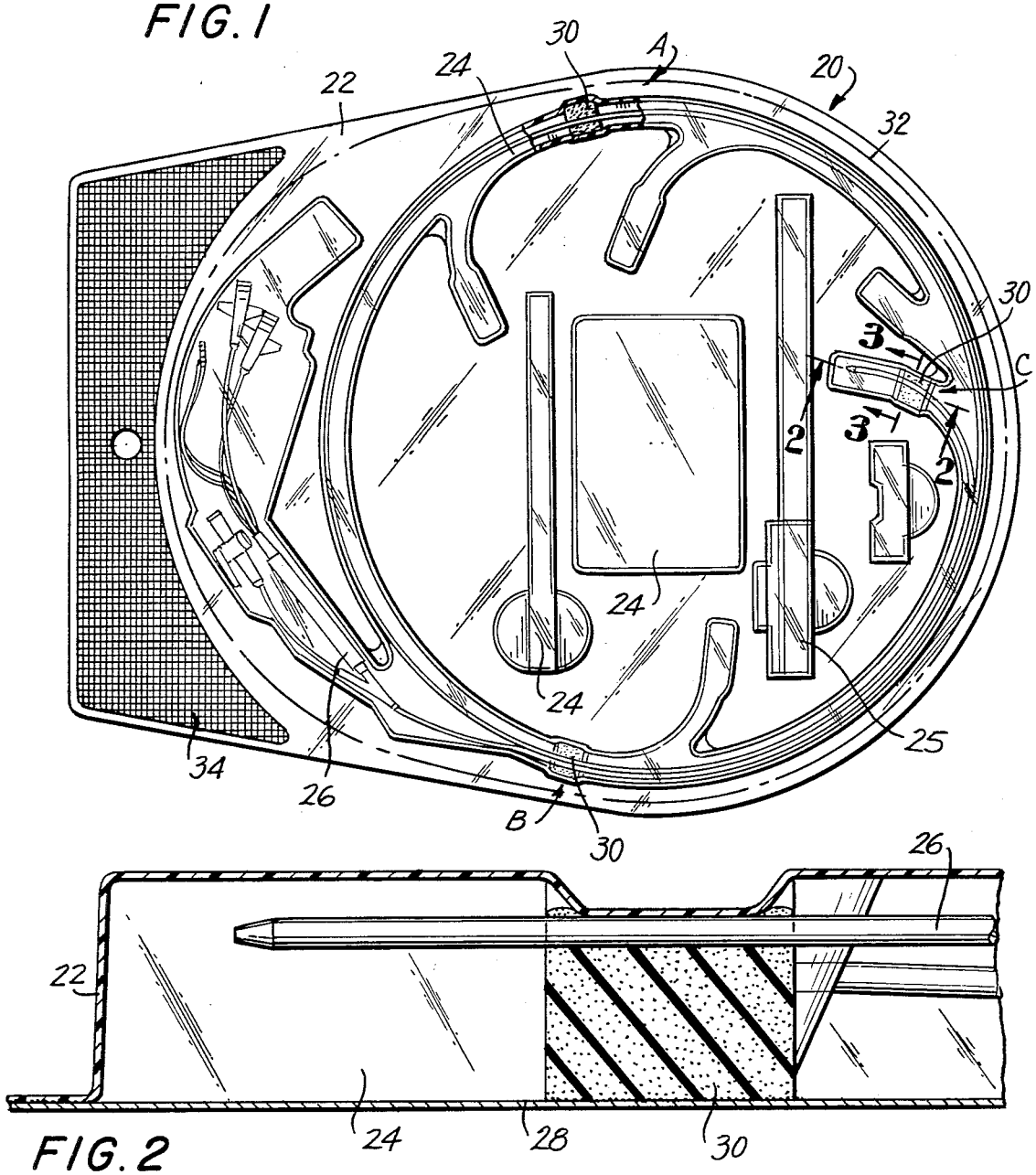
FIG. 1 is a top plan view of a medical device container made in accordance with the present invention.

With continuing reference to the accompanying drawings wherein like reference numerals designate similar parts throughout the various views, reference numeral 20 is used to generally designate the medical device container or blister package constructed in accordance with the concepts of the present invention. The package may be considered a blister package and includes a substantially rigid tray 22 which is preferably thermally formed of any suitable plastic material such as a polyvinyl chloride (PVC). It is within the scope of the present invention, however, that the tray 22 may be of any suitable material such as paper, cardboard, metal or the like which may be manufactured with suitable depressions 24 to receive the device to be contained. In the preferred embodiment, the tray 22 is of a substantially clear plastic which is amber tinted, or includes other suitable ultraviolet screens or filters, which prevents the transmission of ultraviolet light therethrough enabling the product to be stored in full daylight without discoloration or deteriortation of the contents.

The depressions or channels 24 which are formed in the tray 22 may be of any suitable shape and size to completely receive a medical device such as a catheter 26, as shown in the drawings, as well as related and associated items like syringes and the like. The channels 24 are preferably formed in the thermoplastic material by the use of vacuum forming or the like, but may be pressed therein depending on the material from which the tray is manufactured. Preferably, when there is more than one channel 24 to receive various components, each channel is independently formed that is, not continuous, and each channel may then be independently sealed.

The present invention is particularly suited for containing elongated catheters which may be in the area of three feet long, and accordingly the preferred package has a substantially circular channel into which a catheter 26, or the like, may be coiled, thereby replacing long, awkward and flexible prior art packages that required such a medical device to be shipped, stored and handled at its full length.

It is important that the tray 22 be formed of any suitable material which is compatible with the product to be contained and which can maintain a hermetically sterile environment. Polyvinyl chloride (PVC) is particularly well suited, in this regard, and is a preferable material as it is readily formed by vacuum forming and is adapted for heat sealing a backing membrane or sheet thereto.

A pliable or flexible backing sheet or membrane 28 is disposed under the tray 22 and serves to seal off the channels 24 once the sterile workpiece 26 has been disposed therein. The backing sheet 28 is generally coextensive in area with the product tray 22, but may be larger or extend outwardly beyond the tray in order to facilitate handling thereof. It is intended that the backing sheet 28 be heat sealed or bonded by conventional appropriate means to the tray in order to create a sterile seal. A material such as TYVEK (registered trademark) which is a spun-bonded polyolefin membrane, may be heat sealed coated, in order to facilitate thermal bonding to the tray, and used to make the backing sheet 28.

Secured to the flexible backing sheet 28 are at least one, but preferable a plurality of sponge-like or flexible inserts 30 where are preferable made from a closed cell foam. The inserts, preferably in the shape of a cube, but may be of any desired size and configuration such that they are readily disposed into the channel 24 to urge the workpiece into engagement with a portion of the channel 24, and secure it against movement during shipping. The inserts 30 are preferably thermally bonded to the face of the backing sheet on the side facing the tray 22, and may be disposed at any desired location along the channels 24. In the preferred embodiment there are three inserts 30 which serve to secure the catheter 26 in the blister package 20.

The flexible backing 28 is preferably heat sealed to the tray at the outer periphery thereof such that the contents of the package are hermetically sealed from the atmosphere. As is readily apparent from FIG. 1, the backing may be heat sealed to the tray along the irregular dotted line 32 so that all the channels lie within the periphery of the sealed line, or each channel 24 could be separately and independently sealed around the perimeter thereof. At area 34, the backing sheet could be lightly sealed or not sealed at all to the tray to facilitate manual gripping of the backing sheet 28 to facilitate removal thereof by manually peeling it away from the tray 24, as seen in FIG. 4.

Figure 2:
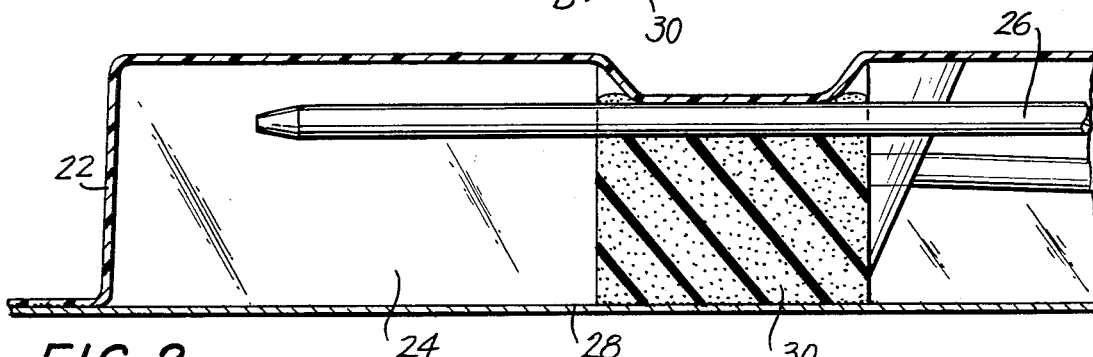
FIG. 2 is a partial cross-sectional view thereof taken along the plane 2—2 in FIG. 1.
Figure 3:
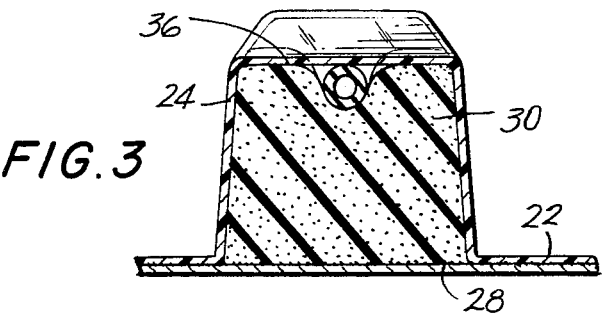
FIG. 3 is a partial vertical cross-sectional view taken along the plane 3—3 in FIG. 1.

With reference to FIG. 2, the channels 24 may contain a depressed region 36 corresponding in location to the inserts, whereby a flexible insert 30 urges the catheter 26 into a firm engagement with portion 36 to retain it from movement during shipping. In order to prevent the insert 30 from displacing laterally, the depressed region 36 is of enlarged width as may be readily seen in FIG. 5. The insert 30 being of a soft closed cell foam material would displace around and about the catheter 26, urging it into engagement with the upper portion of the channel 24 at 36, and would be retained from lateral movement by the surfaces 37 which define the area of enlarged width of the channel 24.

It is also within the scope of the present invention that the insert 30 be a flexible tube or rod 30a, manufactured of a plastic or rubber material, as shown in FIG. 6 and 7. FIG. 7 depicts a hollow tubular portion 30a, but it is within the scope of the present invention that any desired shape, whether hollow or solid, may be used which would properly function to flexibly retain the workpiece in place within channel 24.

The inserts 30 are bonded to the flexible backing 28 so that removal of the backing sheet 28 from the tray 24 pulls the foam inserts 30 from the channel 24 thus releasing the catheter 26 and allowing it to fall freely onto a sterile field in any desired location, without manual contact. The channels 24 are shaped and dimensioned such that there is no pressure or form fit between the medical device contained or received therein so that without the presence of the insert 30, the workpiece is loosely contained or received by the channel 24. The channel is depicted in the drawings as generally rectangular in cross-section, but may be semicircular, or other shape as desired, and may be of irregular shape such as at 25, to accommodate various odd shaped medical objects.

In use, when the package is disposed upside down such that the backing sheet 28 faces downwardly, sheet 28, starting at location 34 may be peeled away from the tray 24 and the catheter 26 would be allowed to partially fall freely downwardly from the package, but not slip completely out due to the pressure of inserts 30 at locations A and B. As soon as the sheet is pulled beyond locations A and B the catheter would be further released and only retained in the tray until the backing sheet 28 is removed beyond location C.

As is readily apparent, the number and locations of the inserts 30 may be varied and arranged to facilitate the free fall of any desired medical instrument. Depending on the location, shape, size and weight of the instrument, the inserts 30, in connection with the shape of the channel, would be located to provide a smooth and even free fall as the package is opened.

The overall size and shape of the tray 24 would be made to correspond to the instruments to be contained, and flexible elongated items such as catheters could be coiled, without damage, and received in a circular channel. The location of the inserts and the number used could be varied from item to item.

Manufacture of the blister package 20 of the present invention includes the forming of channels 24 in the thermoplastic tray by the use of vacuum forming or the like, and if desired, the tray may be labeled by the use of silk screening or pressure sensitive labels, prior to the tray being charged with the medical device. The blister or tray 22 could then be machine or hand loaded with the proper product and the foam cubes 30 pressed into the channel 24 at the locations, A, B and C. The flexible backing sheet 28, which is preferably of a heat sealable material, is heat sealed to the tray by the use of suitable apparatus, such as by using a platen, or the like, which causes the backing sheet 28 to adhere to the tray 22, and the backing sheet 28 is also simultaneously bonded to the inserts 30. The backing sheet 28 and inserts 30 may require a heat seal coating to facilitate the bonding process. It is also within the scope of the present invention that suitable adhesive or the like be utilized to bond the backing sheet 28 to the tray and inserts 30 to the backing sheets 28. All the forming and sealing operations as described may be effected with conventional means as known to those skilled in the art.

The entire manufacturing process can take place within a sterile environment, or the package and its components subjected to sterilizing gases, radiation or suitable heat and pressure as required considering the components and workpiece to be packaged.

A latitude of modification, substitution and change is intended in the foregoing disclosure, and in some instances, some features of the present invention may be employed without a corresponding use of other features.

What is claimed is:

1. A container for elongated flexible sterile medical devices comprising a substantially rigid tray having at least one elongated depression sized and shaped for receiving said device without a pressure fit, a flexible backing sheet which is at least partially bonded to said tray to seal said device within said depression, at least two flexible inserts affixed to said backing sheet in spaced relation on the surface of said backing sheet facing said tray, said inserts being sized and shaped for insertion into said depression at separate spaced locations to urge said device into engagement with at least two discrete portions of said depression whereby said backing sheet may be manually peeled away from said tray with said inserts attached thereto such that at least two said inserts are pulled out of said depression sequentially and disengage said device sequentially and allow same to fall in a controlled manner without manual contact being necessary.

2. A container as in claim 1, wherein the tray is of a plastic material.

3. A container as in claim 2, wherein the plastic contains an ultraviolet filter.

4. A container as in claim 1, wherein said channel has a portion of reduced height at each location adjacent said inserts.

5. A container as in claim 1, wherein said channel has a portion of expanded width at each adjacent said inserts.

6. A method of manufacturing a medical device container comprising the steps of forming at least one depression in a substantially rigid tray, said depression shaped and sized to receive said device without a pressure fit, inserting said medical device into said tray, bonding at least two flexible inserts onto the face of the flexible backing sheet in spaced relation, and bonding said backing sheet to said tray at least along the outer periphery of said channel.

7. A method as in claim 6, further including sterilizing said tray and said backing sheet prior to said bonding step.

8. A method as in claim 6, wherein said tray is formed of plastic by vacuum forming.

9. A method as in claim 6, wherein the insert is bonded to said backing sheet simultaneously with the bonding of said sheet to said tray.

* * * * *